United States Patent [19]
Colin et al.

[11] Patent Number: 5,988,197
[45] Date of Patent: Nov. 23, 1999

[54] FREEZE VALVE AND TREATMENT ENCLOSURE CONTROLLED BY AT LEAST ONE SUCH VALVE

[75] Inventors: Bruno Colin, Marcy L'Etoile; Bernard Mandrand, Villeurbanne, both of France

[73] Assignee: Bio Merieux, Marcy L'Etoile, France

[21] Appl. No.: 08/598,607

[22] Filed: Feb. 12, 1996

[30] Foreign Application Priority Data

Feb. 13, 1995 [FR] France ................................. 95 01802
Feb. 28, 1995 [FR] France ................................. 95 02541

[51] Int. Cl.[6] .............................. F17D 1/18; F16K 49/00
[52] U.S. Cl. ...................... 137/13; 137/251.1; 137/341; 137/828
[58] Field of Search .................. 137/13, 251.1, 137/341, 828

[56] References Cited

U.S. PATENT DOCUMENTS

| 338,447 | 3/1886 | Snee .......................................... 137/13 |
| 3,712,322 | 1/1973 | Cleary ....................................... 137/828 |
| 4,082,109 | 4/1978 | Sun et al. .............................. 137/13 X |
| 4,203,472 | 5/1980 | Dulaney ................................... 137/828 |
| 4,766,922 | 8/1988 | Kaartinen et al. .................. 137/828 X |
| 4,989,626 | 2/1991 | Takagi et al. ........................ 137/828 X |
| 5,101,848 | 4/1992 | Kojima et al. ....................... 137/828 X |

FOREIGN PATENT DOCUMENTS

| 2 663 040 | 12/1991 | France . |
| 43 36 283 A1 | 4/1995 | Germany . |
| WO 90/04927 | 3/1990 | WIPO . |
| WO 94/21955 | 9/1994 | WIPO . |

*Primary Examiner*—John Rivell
*Attorney, Agent, or Firm*—Oliff & Berridge, PLC

[57] ABSTRACT

A freeze valve for a substantially single-phase fluid contains a pipe designed to receive fluid in a flow area, a cold source and a heat source. The cold source and the heat source are placed in thermal contact with the pipe. The pipe is positioned in relation to the cold source and the heat source in such a way so as to permit the freezing of fluid passing through the pipe, thereby closing the passage through the pipe, or the heating of the fluid, thereby opening the passage. The pipe contains, for example, a metallic material that is mechanically strong and capable of dissipating heat by the Joule effect.

6 Claims, 5 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:1:

TCTACGCATT TCACCGCTAC AC      22

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:2:

TCTAATCCTG TTTGCTCCCC      20

(2) INFORMATION FOR SEQ ID NO:3:

-continued

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

ATCTTGACAT CCTCTGACCC                                          20

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

TCGACGGCTA GCTCCAAAT                                           19

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

ACCACCTGTC ACTCTGTCCC                                          20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

GAAGGGGAAA ACTCTATCTC                                          20
```

FREEZE VALVE AND TREATMENT ENCLOSURE CONTROLLED BY AT LEAST ONE SUCH VALVE

FIELD OF THE INVENTION

The present invention relates to a freeze valve for a substantially single-phase fluid.

By "fluid" is meant any substance or material capable of flowing, and of adopting at least two extreme physical forms, one being solid when it is cooled and the other being liquid or viscous when it is heated to room temperature. A fluid according to the invention can be either a liquid or a substance having a greater viscosity, single-phase or two-phase (a more liquid solid, for example), making it relatively viscous for example. The substances or materials in question according to the invention can be either pure substances or varied or complex mixtures containing various chemical, biochemical or biological compounds or components. By way of example, according to the present invention, the fluid in question will, for example, be a biological specimen such as a cell culture in aqueous medium.

BACKGROUND

In accordance with documents U.S. Pat. No. 4,989,626 to Takaki et al. and U.S. Pat. No. 5,101,848 to Kojima et al., a static freeze valve for a fluid has already been described and proposed which comprises:

an element of pipe designed to receive said fluid in the flow area of said pipe, the wall of which is thermally conductive;

one and the same heat source consisting of a Peltier-effect thermoelectric element arranged on the underside of the element of pipe and generating, in a controlled and alternating manner, heat and cold; this heat source is placed in thermal contact, especially by heat exchange, with said element of pipe in order to pass alternately and in a controlled manner, depending on the operation of the thermoelectric element, from a cold state, in which the fluid is capable, by freezing, of sealing off the passage through said element of pipe, to a hot state, in which said fluid is liquefied, thereby freeing said passage.

According to this document, the thermal source is therefore transferred to the outside of the element of pipe that is to be controlled as a valve.

Moreover, in this case the hot and cold sources are coincident in one and the same thermal source, which thus constitutes a parasitic mass which has to be cooled and heated alternately before transferring, respectively, cold and heat toward said element of pipe.

Overall, such a valve exhibits a relatively high thermal inertia which makes it difficult to achieve relatively short response times in order to pass from the open state to the closed state, or back again, limiting or preventing its use as a substitute for a conventional valve, for example a valve of the electromechanical type.

SUMMARY OF THE INVENTION

The subject of the present invention is therefore a static freeze valve exhibiting a relatively low thermal inertia and consequently relatively short response times, both on opening and on closing.

In accordance with the present invention, in combination:

(a) said element of pipe is obtained from a material, especially a metallic material, which is mechanically strong and capable of dissipating heat within itself in a controlled manner by the Joule effect, in order to constitute a hot source directly within its mass;

(b) a cold source, separate from said hot source, designed and controlled to generate only cold, remains alone on the outside of said element of pipe, in thermal contact, especially by heat exchange, with said element of pipe.

By virtue of the previously defined choices according to the invention, it is possible to obtain virtually instantaneous operation of the static freeze valve, especially by incorporating with the above arrangements the following ways and means, in combination:

the cold source constitutes, or is chosen as, an immobile or moving refrigeration reservoir which is relatively large compared to the amount of cold necessary for the valve to pass from the hot state to the cold state;

and the heat dissipated by the Joule effect in the element of pipe is controlled at a relatively high value, at least equal to that necessary to annul or annihilate, temporarily and locally in the region of the valve, the cold transferred by the cold source toward the element of pipe, in addition to the heat necessary to make the valve pass from the cold state to the hot state.

By virtue of the invention, a static freeze valve is additionally obtained in which the interior, that is to say the surface in contact with the fluid used to close the freeze valve, can be incinerated under the effect of the heat released by the Joule effect, for example up to 600° C. Such a characteristic is completely impossible, and consequently absent, in the solutions proposed by documents U.S. Pat. Nos. 4,989,626 and 5,101,848. This characteristic is of great advantage, especially in the field of biological analyses, since it makes it possible to go beyond mere sterilization by eliminating all traces of any biological specimen or material capable of contaminating either the environment or the interior of the pipe, for example during a subsequent biological analysis.

According to the invention, it is possible to have a pipe the two ends of which each form an element of pipe belonging to a static freeze valve according to the invention and, consequently, are each associated both with a cold source and an electrical source. In this way, a confinement or confined enclosure is obtained which is controlled respectively at its two ends for the passage of a fluid, exhibiting the feature, on the one hand, of being able to offer the same cross-sectional flow area from one end to the other, including at the locations where the valves are, and, on the other hand, of being completely incinerable on the inside, for example at up to 600° C. Such a confinement enclosure may be particularly useful for various treatments, especially biological treatments, for which it is necessary both to preserve the biological material which is used and to sterilize the walls that have been in contact with this same material.

The above defined freeze valve and the confined enclosure controlled by said valves are particularly well suited to any automated process for treating any fluid, in particular a biological specimen containing protein or nucleic acid for example. One or more freeze valves according to the invention, and one or more confinement enclosures, especially treatment confinement enclosures, as defined above, may be integrated into various setups, as will be described hereinbelow, and be used in various treatment protocols, especially automated treatment protocols using any sequence of elementary operations which are performed on the same setup.

By "treatment" in the sense of the present invention, is meant any operation or action having the effect of modifying or transforming a fluid specimen. It may be either a physical treatment or a chemical treatment, or any other treatment; it may, for example, be a cell lysis treatment due to the effect especially of high pressures, making it possible to release the cell components, such as nucleic acids, proteins, etc.

BRIEF DESCRIPTION OF THE DRAWINGS

The present invention will now be described with reference to the appended drawing, in which.

DETAILED DESCRIPTION OF THE PREFERRED EMBODIMENTS

Figure 1:
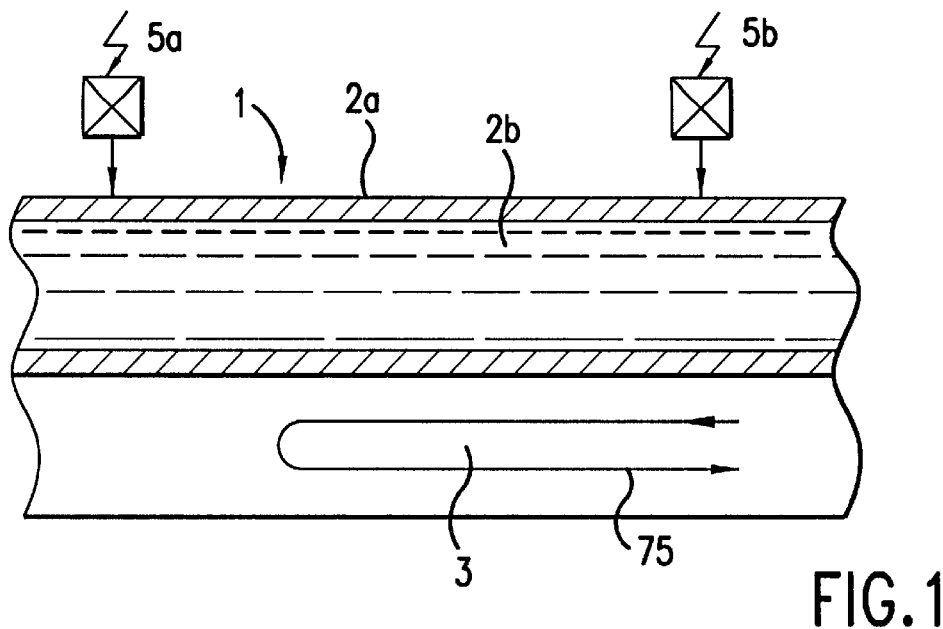
FIG. 1 diagrammatically represents a static freeze valve according to the invention.

In accordance with FIG. 1, a static freeze valve 1 for a single-phase fluid, for example a liquid biological specimen, comprises an element of pipe 2a designed to receive said specimen over practically its entire flow area, this flow area being identical, in shape and size, from one end of the element of pipe to the other. The pipe 2 to which the element 2a belongs is obtained from a material, especially a metallic material, which is mechanically strong and capable of dissipating, within itself, heat by the Joule effect. This material may be a material other than a metallic material, for example a composite, and incorporate a component having a high electrical resistivity. A cold source 3, comprising a serpentine coil 75 for the circulation of a refrigerant, is placed in thermal contact, namely by heat exchange, with the element 2a of pipe. The temperature and refrigerating capacity of the cold source are adapted to the freezing of the fluid across the passage 2b in the element of pipe 2a; thus, if the biological specimen is aqueous, the refrigerant is conventionally a fluoroalkane. Heat generated by an electric current is provided directly within the mass of the element of pipe 2a. An electrical source 5 constituted by two terminals 5a and 5b with switches (not shown) are connected to the element of pipe 2a in order to pass through the latter, in a controlled manner, the electric current and thus generate a hot source. According to the above description, it should be noted that the cold source 3 is separate from the hot source resulting from the Joule effect, is assigned just to producing cold and remains alone on the outside of the element of pipe 2a. The element of pipe 2a is dimensioned in relation to the aforementioned hot and cold sources 3 in order to pass rapidly, for example within a time interval of less than 10 seconds, and preferably less than 1 second, from a cold state, in which the fluid is capable by freezing of sealing off the passage through the element of pipe 2a, including with respect to relatively high internal pressures, for example at least equal to 50 bar, especially 150 bar, to a hot state, in which this same fluid is liquefied, freeing the passage 2b in the element of pipe 2a.

Although composites cannot be excluded, the material of the element of pipe 2a is preferably a metal alloy, for example of the copper—nickel type.

The element of pipe 2a has a thickness of between 1 μm and 50 mm, preferably between 0.001 mm and 2 mm, and advantageously between 0.1 and 2 mm. The element of pipe 2a also has an internal cross section at most equal to 50 mm and is preferably of the capillary type so as to have an internal cross section of between 0.001 mm and 2 mm.

In order to obtain the same static freeze valve according to the invention in a manner not shown in the appended drawing, and according to an alternative embodiment of the invention, the element of pipe 2a is placed within a cold source 3, constituting a refrigeration reservoir which is relatively large compared to the amount of cold for the valve to pass from the hot state to the cold state, for example in a refrigerating enclosure containing a liquid refrigerant, for example ethylene glycol, which is itself cooled by a refrigerating circuit, but which has a relatively low refrigerating capacity; whereas the heat dissipated by the Joule effect in the element of pipe 2a is controlled at a relatively high value, at least equal to that necessary to annul, temporarily and locally in the region of the valve, the cold transferred by the cold source to the element of pipe, in addition to the heat necessary for the valve to pass from the hot state to the cold state.

The relatively large refrigeration reservoir may be obtained in another way, for example by continually circulating a liquid refrigerant in a circulation pipe, in heat exchange with the element of pipe of the valve.

In accordance with the present invention, in an elementary control step, and virtually instantaneously, the immobile or moving fluid, received in the element of pipe 2a, is controlled successively:

by freezing the fluid across the passage 2b, by virtue of the cold source 3, in order to block off the element of pipe 2a and consequently close the pipe 2; and by passing an electric current through the mass of the element of pipe 2a, dissipating heat by the Joule effect, the heat being transferred directly to the fluid, and melting the frozen fluid across the passage 2b, freeing the latter and consequently opening the valve 1.

In conclusion, in the manner of a solenoid valve, a freeze valve according to the invention can be opened or closed at will simply by controlling the passage of an electric current through the element of pipe 2a. This in particular makes its control particularly easy compared to that of a Peltier-effect thermoelectric element.

Consequently, in the description hereinbelow, opening and closing a valve according to the invention will be understood to mean, respectively, the previously described operations of, respectively, liquefying and freezing the fluid present in the element of pipe.

Figure 2:
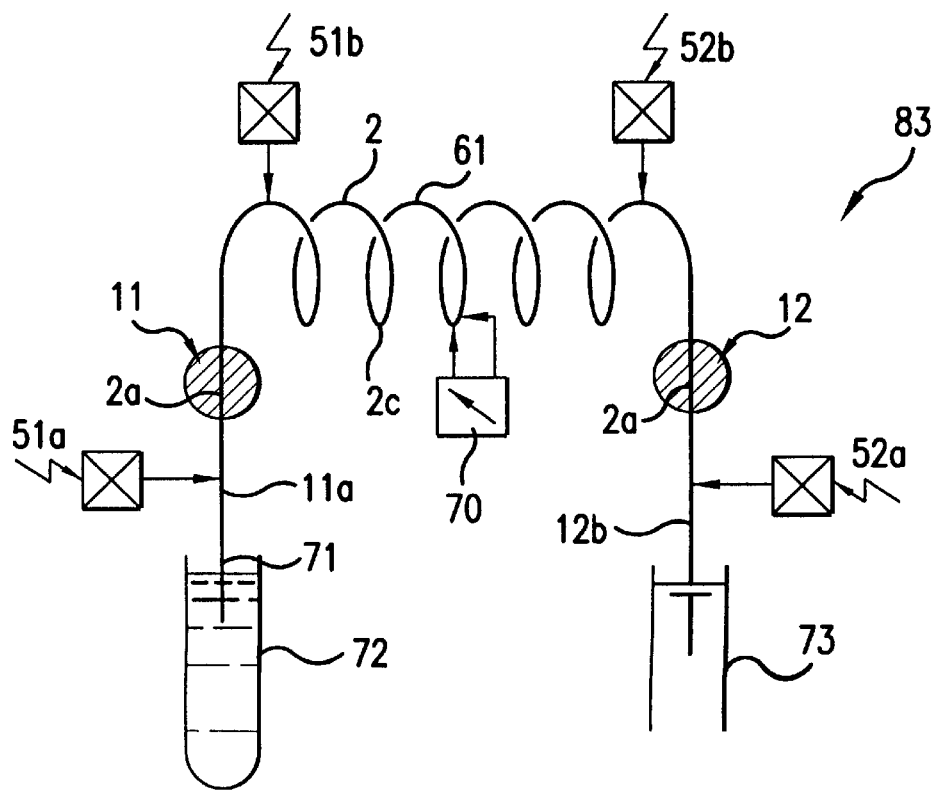
FIG. 2 represents a setup which includes an elementary treatment enclosure according to the invention.

In accordance with FIG. 2, an elongate elementary treatment enclosure 83 is obtained from a pipe 2, namely a metal tube wound in a coil 61, two end elements 2a of which are each associated both with a cold source and an electrical source, respectively 51a/51b and 52a/52b, in order to constitute, respectively, two valves 11 and 12 according to the invention.

Because of the electrical setup explained previously, an electrical source, in this case 51b/52b, is connected to the confined portion 2c of the pipe 2 lying between the two valves 11 and 12, in order to pass through said portion an electric current which dissipates heat directly in said pipe by the Joule effect.

The elementary treatment enclosure 83 and its control valves 11 and 12, constitute one and the same pipe having the same internal cross section along its entire length.

Of course, in a manner not shown, single electrical source may be connected both to the confined portion 2c of the pipe 2 and to the elements of pipe, 2a belonging to the two valves 11 and 12, respectively. Moreover, electrical connection means (not shown) are designed to pass an electrical current through this confined portion 2c and/or the elements of pipe 2a, in a controlled manner, in any pre-established sequence of elementary electrical connections of the confined portion 2c and/or of the elements of pipe 2a. For example, these electrical connection means comprise at least one electrical terminal or contact with the pipe 2, designed so as to move in the direction or length of the latter, in order to include the confined portion 2c and/or the elements of pipe 2a, in a controlled manner, in an electrical circuit.

In the same manner, each static freeze valve 11 and 12 can be moved along the direction or length of the pipe 2 by arranging, in a movable manner, a cold source 3 and/or the electrical contacts 51a/51b, 52a/52b along the pipe 2.

In the direction of flow of a biological specimen to be treated, from the left to the right in FIG. 2, the inlet 11a of the valve 11, and consequently the upstream part, is connected to a sampling means 71 for taking up the specimen from a tube 72, and the outlet 12b of the valve 12, and consequently the downstream part, is connected to a flow causing means 73 for propelling or pumping the specimen. Means 70 are provided for controlling the pressure and/or temperature in the confinement zone 2c.

By virtue of the arrangements shown in FIG. 2, the two valves 11 and 12 according to the invention define a confinement portion or zone 2c and the two valves 11 and 12 control the passage of the fluid treated in the aforementioned zone 2c. Moreover, by passing an electric current through the mass of the pipe 2, heat is dissipated by the Joule effect directly in the confinement zone 2c, which heat is transferred directly to the treated fluid, therefore increasing the temperature and/or pressure of said treated fluid in relation to the amount of heat thus transferred.

The setup according to FIG. 2 can be used for a cell lysis in the following manner:

by actuating the pump 73 and by the sampling means 71, a specimen, especially one from a sample or a cell culture, is sucked up into the pipe 2, filling in particular the confined portion 2c;

the valves 11 and 12 are closed in succession in such a way that the specimen is trapped between the valves 11 and 12;

an electric current is passed between the terminals 51b and 52b, in a controlled manner, through the confined portion 2c, which raises the temperature and consequently the pressure in the zone 2c, the consequence of which is to lyse the cells contained in the treated fluid; and by opening the valves 11 and 12, the treated specimen is recovered.

The flow-causing means 73 may be dispensed with by operating in the following manner:

with the valves 11 and 12 open, an electric current is made to flow through the confined portion 2c in such a manner that the pipe 2 heats up and is emptied of its air;

this electrical flow is stopped, the valve 12 is closed and the tube 2 is cooled in such a way that a partial vacuum is created in the tube 2, this partial vacuum having the effect, if the sampling means 71 is immersed in a liquid specimen in the tube 72, of drawing said specimen by suction into the confined treatment portion 2c; and the treatment then continues as previously, after closing off the valve 11.

Figure 3:
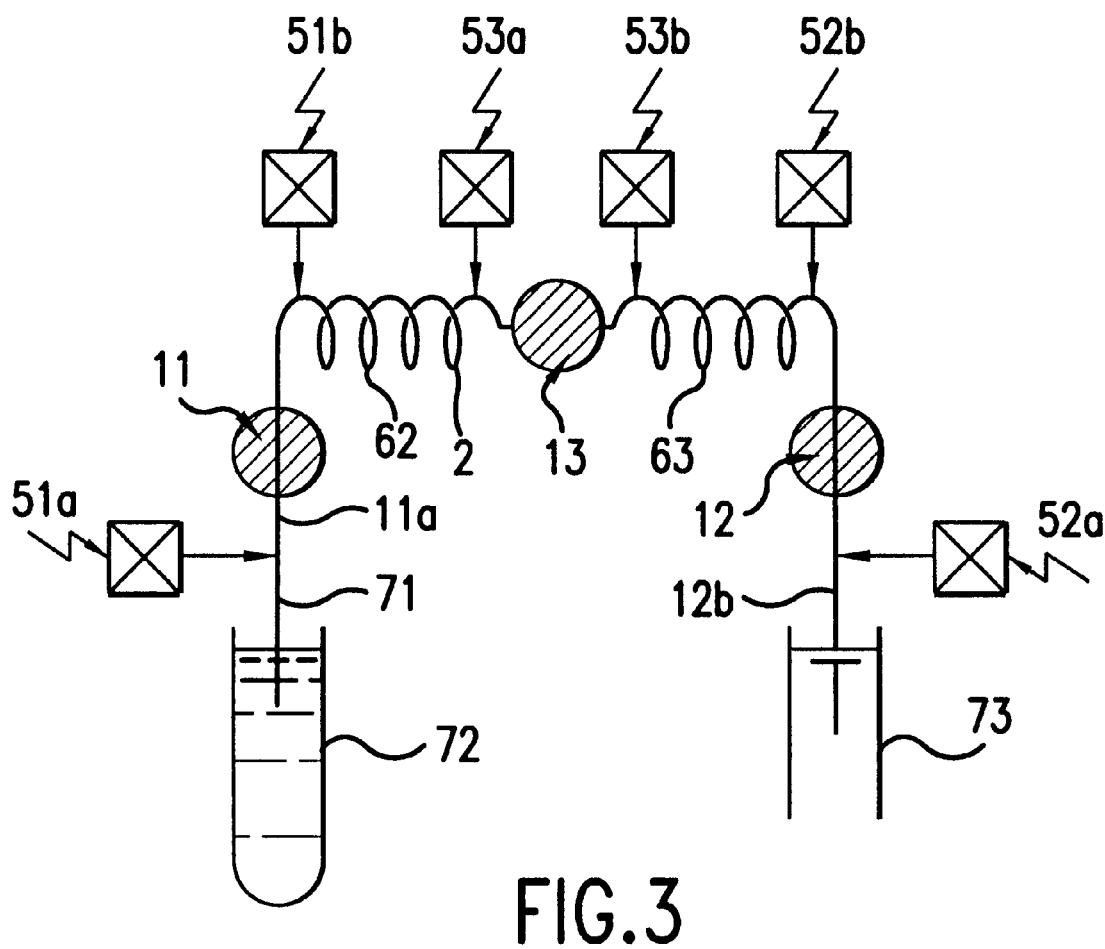
FIGS. 3 and 4 represent two other setups, each combining several elementary treatment enclosures according to the invention.

In accordance with the setup in FIG. 3, two enclosures 62 and 63 are placed in series and separated from each other by a static freeze valve 13 according to the invention. This valve 13 itself may be provided with a throttling neck (not shown), that is to say a flow area smaller than the rest of the pipe 2.

The static freeze valve 13 is controlled by the electrical terminals 53a and 53b while the electrical supply of the enclosures 62 and 63 may be controlled respectively by the electrical terminals 51b and 53a, and 53b and 52b.

The setup in FIG. 3 may be operated in the following manner, again for lysing a specimen, especially from a sampling or a cell culture:

(a) with the valves 11, 12 and 13 open, a specimen is sucked up into the pipe 2 by the flow causing means 73, and the valve 13 is closed followed by the valve 11;

(b) by applying an electrical current to the enclosure 62, the temperature and/or pressure of the treated specimen is raised, as previously;

(c) the valve 12 is closed and the valve 13 opened, in such a way that the treated specimen is propelled through the throttling neck provided in the valve 13, from the treatment enclosure 62 to the treatment enclosure 63;

(d) by closing the valve 13 and applying an electric current to the enclosure 63, the temperature and hence the pressure in the enclosure 63 are raised again;

(e) with the valve 11 remaining closed, by opening the valve 13, the treated specimen is again propelled, from the enclosure 63 to the enclosure 62, through the throttling neck of the valve 13;

(f) and so on, if necessary.

A particularly effective cell lysis is thus obtained.

The setup in FIG. 3 can be used in another way, according to which the enclosure 62 serves as a treatment enclosure and the enclosure 63 as an enclosure for capturing a biological constituent of the treated specimen, for example a nucleic acid. For this purpose, the internal walls of the pipe 2 in the enclosure 63 are treated beforehand, for example with any specific ligand or antiligand of the biological material to be captured, for example antibodies, oligonucleotides, proteins, peptides, etc.

The setup in FIG. 3 is, in this case, still used as described previously, except that step (d) is used to capture the biological constituent, and therefore to deplete the treated specimen of said constituent, and, during step (e), the treated specimen is extracted via the valve 12.

After the capture enclosure 63 has been washed one or more times, the biological constituents are released into a volume smaller than the initial specimen volume, making it possible therefore to enrich, with said desired biological constituent, the final specimen to be treated.

The cell lysis in the enclosure 62 may be carried out by means other than by heating, for example by applying ultrasound within the enclosure 62.

Various optical, electrochemical or radioactive detection systems may be associated with the enclosures 62 and 63.

Figure 4:
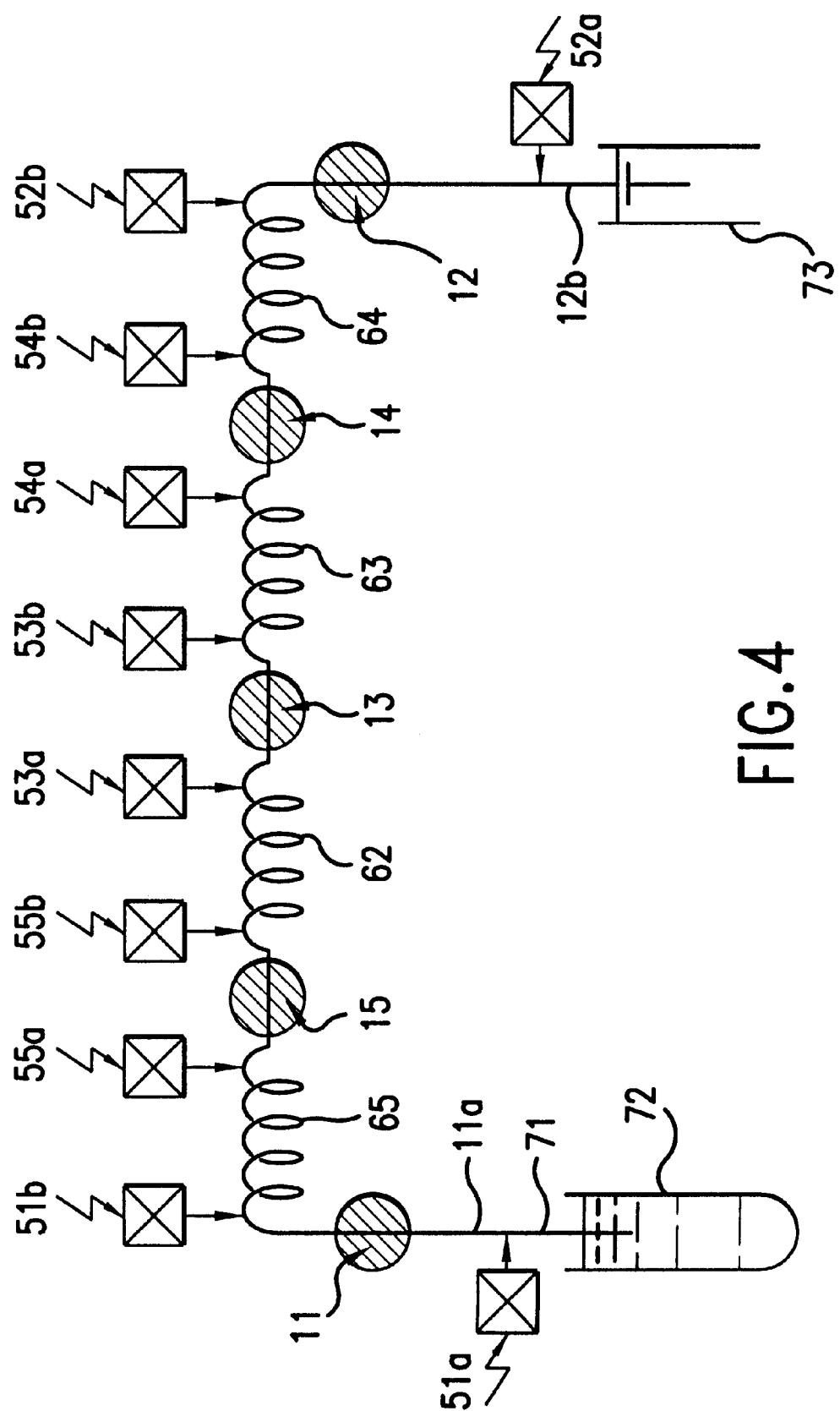

The setup in FIG. 4 combines in series four treatment zones according to the invention, respectively, from the left to the right in said FIGS., 65, 62, 63 and 64, these being separated by valves according to the invention, namely respectively 11 and 15, 15 and 13, 13 and 14, and 14 and 12. As mentioned previously, each of these enclosures may be heated by passing an electric current. Such a setup proves to be particularly useful when the biological specimen treated must not be heated or subjected to particularly high pressures. In order to do this, the following operation is then carried out by means of the pump 73:

sucking up into and confining in the enclosure 62, between the two closed valves 15 and 13, a biological specimen;

sucking up into and confining in the zone 65, between the valves 11 and 15, another fluid, in this case a neutral liquid such as water or a buffer;

heating the enclosure 65 in order to increase the pressure of the neutral liquid in the enclosure 65;

closing the valve 14 and opening the valves 13 and 15, in such a way that the biological specimen is pushed through the valve 13, possibly provided with a throttling neck, by the neutral liquid in the enclosure 65, from the enclosure 62 to the enclosure 63;

sucking up into and confining in the enclosure 64, between the closed valves 14 and 12, a neutral liquid as before; heating this liquid by passing an electric current through the enclosure 64;

closing the valve 15 and opening the valves 14 and 13, in such a way that the biological specimen is pushed through the valve 13, from the enclosure 63 to the enclosure 62, due to the effect of the highly pressurized neutral liquid present in the enclosure 64;

and so on, taking into consideration the appropriate opening or closing of the valves previously and respectively in question.

Figure 5:
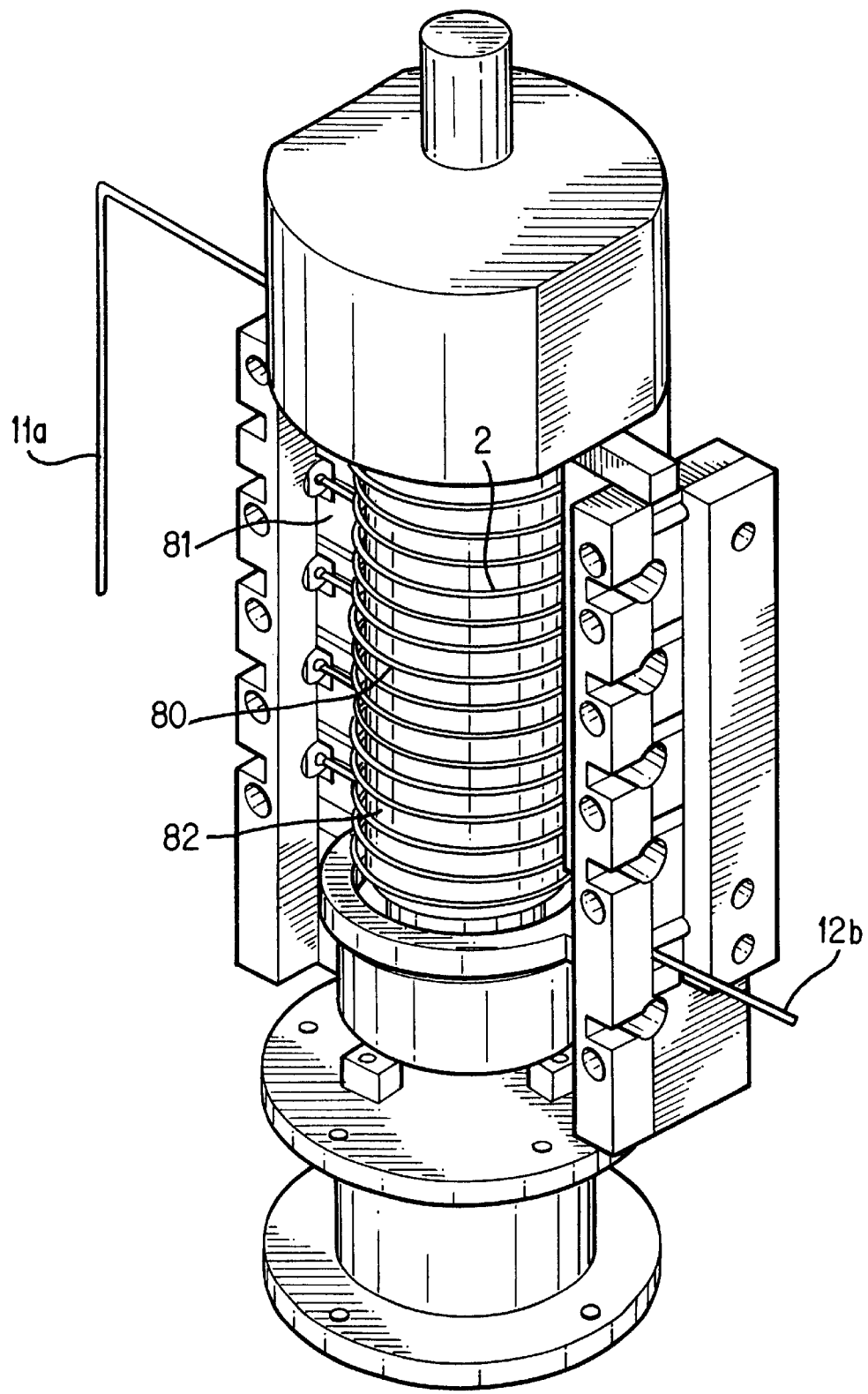
FIGS. 5 and 6 represent an experimental setup which has enabled the principles of the present invention to be tested, this setup being shown in exploded view in FIG. 5 and as an electrical diagram in FIG. 6.
Figure 6:
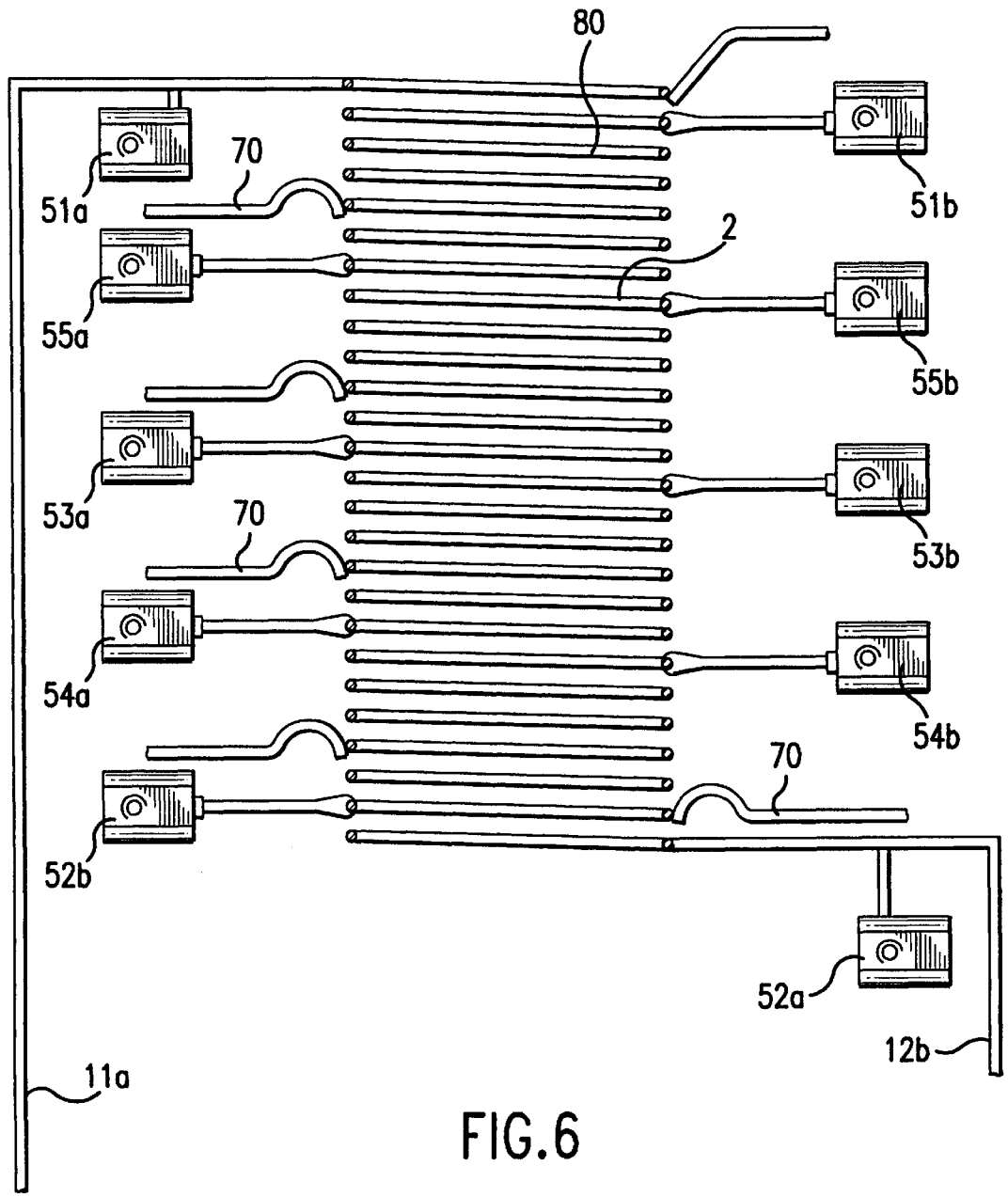

The experimental setup in FIGS. 5 and 6 corresponds to the simplified diagram in FIG. 4, in such a way that the common numerical references denote the same elements or means. A single metal pipe 80, in the form of a serpentine coil combining in continuity of flow the enclosures 65, 62, 63 and 64, is placed vertically inside a thermally insulated chamber 81. Another serpentine coil 82, for the continuous circulation of a liquid refrigerant, is placed in the same chamber 81, so as to exchange heat with the pipe 2 in the form of the serpentine coil 80, the turns of the serpentine coil 82 being wound in an adjacent manner to those of the serpentine coil 80. Only the inlet tube 11a, the outlet tube 12b, various thermal probes 70 in the form of thermocouples, and the electrical terminals corresponding to the relays 51a and 51b, 55a and 55b, 53a and 53b, 54a and 54b, 52a and 52b, go into the chamber 81.

Electrical connection means, not shown, establish connection to the aforementioned electrical connection terminals or relays, in order to include the various confined portions 65, 62, 63 and 64 and the various elements of pipe constituting the freeze valves, in a controlled manner, in an electrical circuit, depending on the treatment process adopted for the biological specimen introduced via the inlet tube 11a and removed, completely treated, via the outlet tube 12b.

EXAMPLE

Lysis of a *Staphylococcus epidermidis* isolate

A strain of *S. epidermidis* isolate has been tested for lysis with the test assembly described with the reference to FIGS. 5 and 6, but restricted to a single treating enclosure according to FIG. 2. A fresh bacterial night culture was OD-numerated and a range of 10-fold dilution was tested and analyzed for the presence of nucleic acids before and after lysis in the test assembly.

Lysis in the test assembly was performed as follows:

The test assembly was brought to room temperature, 2 mls of the bacterial suspension to test were pushed into the capillary tube 2. After the tube has been frozen by default down −20° C. (i.e. the whole bacterial suspension is frozen), the internal section of the tube is heated to 100° C. for 5 sec whereas the two extreme section 11 and 12 remain frozen and thus constitute two valves that delimit the lysis reaction chamber. The internal section is then frozen again for 5 sec. After heating to room temperature, what has now become a lysate is recovered by pulling it out and analyzed for the presence of nucleic acids. Reuse the tube for a new assay imposes a molecular sterilization, or incineration, achieved as follows: the tube is washed by pushing 3 mls of distilled water, emptying the tube and finally heating it along its whole length for 5 sec at 400° C.

Analysis for nucleic acids was performed as follows: from $10^9$ to $10^8$ bacteria/200 µl, the rRNA present in the corresponding lysate was hybridized on the immuno-assay appliance VIDASr (a registered trademark) using a eubacterial capture probe (S8L) and a alkaline-phosphatase conjugated detection probe (E2 20) and the hybridization signal expressed in RFU (Relative Fluorescence Units). From $10^5$ to 1 bacteria/10 µl, the rDNA present in the corresponding lysate was amplified by PCR with primers SPI-1 and SPI-4 and the PCR-product hybridized on the VIDASr using the capture probe SPI-5 and detection probe SPI-6.

The sequences of DNA oligonucleotides was as follows:

S8L: TC TAC GCA TTT CAC CGC TAC AC (SEQ ID NO: 1)

E2 20: TC TAA TCC TGT TTG CTC CCC (SEQ ID NO: 2)

SPI-1: ATC TTG ACA TCC TCT GAC CC (SEQ ID NO: 3)

SPI-4: TCG ACG GCT AGC TCC AAA T (SEQ ID NO: 4)

SPI-5: AC CAC CTG TCA CTC TGT CCC (SEQ ID NO: 5)

SPI-6: GA AGG GGA AAA CTC TAT CTC (SEQ ID NO: 6)

The VIDASr hybridization steps were as follows: at the end of the lysis step in the test assembly, the lysate (200 µl or 10 µl) was placed in the 10-well polypropylene strip of the VIDASr instrument (BioMérieux, Marcy l'Etoile, France). This strip has already been filled with all the necessary reagents for hybridization in separate wells: sample diluent, labelled probe, washing buffer and substrate. The loaded strip was placed into the tracks of the VIDASr and all subsequent steps of the non-radioactive hybridization protocol were performed automatically for 1.5 hours at 37° C. Two DNA oligonucleotides were used in a sandwich hybridization format described in French Patent No. A2 663 040 to Philippe et al. One oligonucleotide was coated inside the solid surface of the pipette tip, the Solid Phase Receptacle (SPRr, a registered trademark) and acted as a capture probe. A second oligonucleotide, covalently linked to alkaline phosphatase, was used as detection probe and targeted 16S rRNA or PCR-amplified rDNA. Upon completion of the assay, the alkaline phosphatase substrate, 4-methylumbelliferyl phosphate, is pumped from the final well which is an optically-clear cuvette. The enzyme catalyzes its conversion into a fluorescent product, 4-methylumbelliferone. The intensity of fluorescence of the cuvette content is measured by the VIDASr optical scanner before and after contact with the SPRr. Results are subsequently analyzed automatically and expressed in RFU (Relative Fluorescence Units) by the computer interface. Test values are generated for each sample by subtraction of the blank value (substrate cuvette reading) from the sample fluorescence. Test values are compared with a cut-off value to yield an interpretation which is then printed by the instrument. Test values of <200 RFU were considered negative results. Tests values greater or equal than 200 were considered positive results and thus, provided evidence of presence of targeted nucleic acids (RNA or rDNA).

The results obtain are as follows:

Analytical method
S. epidermidis inoculum
Hybridization results
(RFU)
non-lyzed
thermal capillary
200 μl - hybridization of natural RNA
10 9
10 8
640
481
6925
5512
10 μl - hybridization of PCR-amplified rDNA
10 5
10 4
10 3
10 2
10
1
0
10 1
94
98
98
94
96
75
4234
5898
7070
10915
7746
2235
185

These results indicate that if some lysis occurs for high inoculum in the non-lyzed data (bacteria resuspended in distilled water: values of 640 and 481 RFU) it is probably due to osmotic pressure which however far less efficient than the lysis by thermal shocks using the capillary tube. For low inoculum of target, lysis, of S. epidermidis is achieved since rDNA is efficiently amplified down to 1 bacteria.

Of course (and this is an advantage obtained according to the invention) each entire setup can be completely sterilized or decontaminated, with respect to any molecular species such as a nucleic acid, after each treatment, especially by passing an electric current through the entire pipe 2, for example from the sampling means 71 to the inlet of the pump 73 according to the setup in FIG. 4, and consequently through all the valves according to the invention and through the confined portions or elementary enclosures according to the invention.

---

What is claimed is:

1. A treatment enclosure, comprising:

at least two valves, each of the at least two valves comprising a pipe designed to receive a fluid and controllably pass said fluid therethrough, said pipe comprising a material that is thermally conductive, mechanically strong and capable of dissipating heat within itself in a controlled manner;

a heat source including at least a segment of said pipe; and a cold source in thermal contact with said segment of pipe, wherein said cold source is separate from said heat source, wherein said cold source and said heat source control the flow of said fluid through said pipe by said cold source withdrawing heat and cooling said fluid in said segment of pipe to a temperature sufficient to freeze said fluid and prevent passage of said fluid through said pipe, and by said heat source heating said frozen fluid to a temperature sufficient to liquify or vaporize said frozen fluid and allow said fluid to pass through said pipe, wherein a first valve of said at least two valves is arranged at a first end of said pipe and a second valve of said at least two valves is arranged at a second end of said pipe, and an electrical source is connected to a first segment of pipe that lies between said first valve and said second valve, and passes an electric current through said first segment in a controlled manner to distribute heat directly in said pipe.

2. The enclosure as claimed in claim 1, wherein said electrical source is connected to at least one additional segment of pipe, wherein said at least one additional segment of pipe comprises at least one valve, and wherein electrical connection members are designed to pass said electric current through said first segment or said at least one additional segment of pipe, in a controlled manner.

3. The enclosure as claimed in claim 2, wherein the electrical connection members comprise at least one electrical contact to said pipe, wherein said electrical contact is capable of moving along said pipe in order to include or exclude said first segment or said additional segment of pipe, in a controlled manner in an electrical circuit.

4. The enclosure as claimed in claim 2, wherein the electrical connection members comprise a plurality of electrical connection terminals distributed along said pipes and electrical connectors arranged with said connection terminals, in order to include or exclude at least one of said first segment and said additional segment of pipe, in a controlled manner in an electrical circuit.

5. A process of selectively confining a liquid in a cylindrical pipe comprising at least two spaced apart segments delimiting between them a confinement zone, a first one of said at least two spaced apart segments being located downstream from a second one of said at least two spaced apart segments, according to a flow direction of said liquid in said cylindrical pipe, the process comprising:

freezing said liquid serially in said first and second spaced apart segments of said cylindrical pipe to prevent passage of said liquid in said cylindrical pipe and to confine said liquid between said at least two spaced apart segments of said cylindrical pipe; and melting said frozen liquid in said first and second spaced apart segments of said cylindrical pipe to allow a portion of said liquid previously confined in said confinement zone to pass through said cylindrical pipe.

6. The process as claimed in claim 5, wherein heat is transferred to said liquid in said first and second spaced apart segments of said cylindrical pipe by passing an electric current through said first and second spaced apart segments of said cylindrical pipe.

* * * * *